US006789467B2

(12) United States Patent
Johnston, Jr. et al.

(10) Patent No.: US 6,789,467 B2
(45) Date of Patent: Sep. 14, 2004

(54) AUTOMATIC POULTRY INJECTION DELIVERY APPARATUS

(75) Inventors: Joseph H. Johnston, Jr., Gainesville, GA (US); Roger Luke, Stone Mountain, GA (US); Robert Pruitt, Lithonia, GA (US); Eric Lust, Grayson, GA (US); David C. McHenry, Stone Mountain, GA (US); Charles O. Phillipi, Monroe, GA (US)

(73) Assignee: Merial Limited, Duluth, GA (US)

( * ) Notice: Subject to any disclaimer, the term of this patent is extended or adjusted under 35 U.S.C. 154(b) by 0 days.

(21) Appl. No.: 10/295,635

(22) Filed: Nov. 14, 2002

(65) Prior Publication Data

US 2003/0198722 A1 Oct. 23, 2003

Related U.S. Application Data

(60) Provisional application No. 60/331,468, filed on Nov. 16, 2001.

(51) Int. Cl.$^{7}$ .......... A23L 1/00; A23L 1/31; A23L 3/00; A61M 5/00

(52) U.S. Cl. .......... 99/532; 99/487; 604/144; 604/152; 604/156

(58) Field of Search .......... 99/487, 516, 345–347, 99/532–535; 118/14, 24, 300; 128/200, 14, DIG. 1; 604/144, 156, 500, 131, 115, 154, 152, 23, 147, 208; 222/262, 263, 324, 327, 333, 383.1; 43/131

(56) References Cited

U.S. PATENT DOCUMENTS

| | | | | | |
|---|---|---|---|---|---|
| 3,636,857 | A | * | 1/1972 | Panek | 99/532 |
| 3,641,998 | A | | 2/1972 | Lyon et al. | |
| 3,964,481 | A | | 6/1976 | Gourlandt et al. | |
| 4,053,963 | A | * | 10/1977 | Matheu | 452/67 |
| 4,108,176 | A | | 8/1978 | Walden | |
| 4,119,022 | A | * | 10/1978 | Dykes et al. | 99/532 |
| 4,177,810 | A | | 12/1979 | Gourlandt | |
| 4,250,959 | A | * | 2/1981 | Spasojevic | 165/61 |
| 4,254,151 | A | * | 3/1981 | Townsend | 426/231 |
| 4,276,879 | A | | 7/1981 | Yiournas | |
| 4,331,071 | A | * | 5/1982 | Niccolls | 99/532 |
| 4,452,132 | A | * | 6/1984 | Miller et al. | 99/483 |
| 4,475,666 | A | * | 10/1984 | Bilbrey et al. | 222/14 |
| 4,515,590 | A | | 5/1985 | Daniel | |
| 4,681,565 | A | | 7/1987 | Gourlandt | |
| 4,758,227 | A | | 7/1988 | Lancaster, Jr. et al. | |
| 4,782,746 | A | * | 11/1988 | Niccolls | 99/532 |
| 4,863,443 | A | | 9/1989 | Hornung | |
| 5,289,762 | A | * | 3/1994 | Phillips | 99/495 |
| 5,312,353 | A | | 5/1994 | Boggess et al. | |
| 5,359,925 | A | * | 11/1994 | Forker | 99/450.8 |
| 6,457,400 | B1 | * | 10/2002 | Hutzler | 99/345 |
| 6,460,481 | B1 | * | 10/2002 | Young | 118/14 |

* cited by examiner

*Primary Examiner*—Timothy F. Simone
(74) *Attorney, Agent, or Firm*—Judy Jarecki-Black; Merial Ltd.

(57) ABSTRACT

The present invention provides systems for the injection delivery of at least two fluid doses to a small bird by penetrating the skin of the recipient bird with at least two injection needles. It is then possible to simultaneously inject drugs, or other fluid vaccines that do not mix well or whose mixture would be detrimental to the stability or efficacy of the active ingredients therein. The present invention provides a novel injection needle support for connecting the injection needles to dose distributors and fluid supply containers while maintaining the injection ends of the injection needles in a substantially parallel arrangement.

The injection needle support typically is attached to a carrier connected to an actuator, an actuator power source and a switch mechanism wherein the actuator, when activated, can reciprocally move the carrier and injection support toward and away from an injection position. The injection delivery system may further include one or more dose distributors and fluid supply containers for delivering fluid doses to the injection needles for injection into a recipient bird held against an aperture in a retaining plate.

13 Claims, 3 Drawing Sheets

AUTOMATIC POULTRY INJECTION DELIVERY APPARATUS

The present application claims the benefit of priority from a provisional application filed Nov. 16, 2001 and having U.S. Serial No. 60/331,468.

FIELD OF THE INVENTION

The present invention relates to a device for the injection delivery of drugs or vaccines to birds. More particularly, the present invention allows the subcutaneous or intramuscular injection of one or two doses of drugs or vaccines into bird.

BACKGROUND OF THE INVENTION

Inoculation of one-day old chicks or other small birds using automatic vaccine injection devices is known in the poultry industry. Automatic bird injection devices, including devices suitable for injecting small bird such as one-day chicks, are described, for example, in U.S. Pat. Nos. 5,312,353, 4,863,443, 4,758,227, 4,681,565, 4,515,590, 4,276,879, 4,177,810, 4,108,176, 3,964,481, 3,641,998. Such automated devices can allow one person to inoculate a multitude of birds with the significant economic benefit of reduced labor costs.

These automatic injection devices generally provide a movable reciprocating carrier that supports a single injection needle assembly connected to a fluid supply container. The carrier may be actuated relative to a support surface against which the chick is maintained by the operator. Once the needle reaches its extended position, and when it has penetrated into the tissue of the bird, a syringe or other dose delivery means is actuated to deliver the required dose from the supply container to the recipient bird.

It may also be desirable to separately administer different drugs or vaccines. U.S. Pat. No. 4,758,227, for example, provides two injection needles configured to be simultaneously introduced into the bird's breast muscle tissue. This automatic injection system can to inject two doses at the same time. However, the diminutive size of intended recipient birds, such as one-day chicks, has limited available automatic injectors to delivering the separate doses to the breast muscle tissue on opposite sides of the keel bone.

Many therapeutic compositions are not stable or otherwise incompatible when co-mingled. Such combinations must be either injected consecutively and/or injected into different localities in the recipient bird. Further, for vaccines or drugs that need to be administered subcutaneously into the necks of one-day chicks, a procedure that requires more precise and limited penetration of the bird than generally is practiced by available automatic injection delivery systems is necessary. Manual injections of the drugs or vaccines is still the only procedure available, with the main drawback of reduced production. Moreover, to inject a second dose of a drug or vaccine, the birds must be rehandled, inducing undue stress in the bird and significant increases in costs.

Thus, there exists a need for an automatic inoculating system for small birds, especially for one-day chicks, that can automatically deliver two or more separate doses of therapeutic fluids such as drugs or vaccines via a subcutaneous route.

SUMMARY OF THE INVENTION

The present invention provides systems for the injection delivery of at least two fluid doses to a small bird by penetrating the skin of the recipient bird with at least two injection needles. It is possible with the injection delivery system of the present invention to simultaneously inject drugs, or other fluid vaccines that do not mix well or whose mixture would be detrimental to the stability or efficacy of the active ingredients therein. Preferably, the injection ends of the injection needles will penetrate the skin of the recipient bird concurrently and deliver the fluid doses to a small target tissue area. The present invention provides a injection needle support for connecting the injection needles to dose distributors and fluid supply containers while maintaining the injection ends of the injection needles in a substantially parallel arrangement to allow for penetration of the bird's skin by both needles.

The injection needle support typically is attached to a carrier operably connected to an actuator, an actuator power source and a switch mechanism wherein the actuator, when activated, can reciprocally move the carrier and injection support toward and away from an injection position. The injection delivery system may further includes one or more dose distributors and fluid supply containers for delivering fluid doses to the injection needles for injection into a recipient bird held against an aperture in a retaining plate. When the carrier and injection needle support are in an extended position, the injection needles attached project through the apertures of the needle support and penetrate a selected area of the skin of the recipient bird. The fluid dose(s) is then delivered through the injection needles to the bird. The injection needle support of the present invention generally comprises a base, a base plate having recesses for receiving hubs of the injection needles, and an end plate having bores for receiving the shank portions of the injection needles. The needle support further comprises fluid connections for delivering fluid doses to the needles and which communicate with the recesses and the hubs of injection needles inserted therein. The shank portions of the needles also may be curved and not bent so that their internal canula sections are substantially maintained and fluid flow is not restricted. The injection ends of the needles generally project from the injection needle support in a substantially parallel configuration and in close proximity to each other to allow the substantially simultaneous penetration of the skin of a recipient bird, but with sufficient separation such that the fluids being administered do not substantially mix or interfere with each other once subcutaneously administered.

The injection ends of the needles also may be beveled. In one embodiment of the present invention, the needles are oriented about their longitudinal axes to face the bevels away from each other, thereby directing the two fluid flows exiting from the injection ends into opposite directions.

In another embodiment of the injection delivery system of the present invention, the injection needles each are operably connected via a fluid connection to a dose distributor, such as a multidose syringe, attached to the injection needle support. Alternatively, the dose distributor(s) may be a large volume multidose syringe that simultaneously provides a fluid supply container. The multidose syringe can be stepwise actuated to deliver a series of consecutive fluid doses. A pump also may be used to deliver the injectable fluid from a fluid supply container, and to expel the required dose from the injection needle. Additionally, the fluid connections can include substantially rigid piping, or can include flexible fluid ducts. The flexible fluid ducts allow the dose distributors to be located on the movable carrier but separate from the injection needle support, or on a fixed part of the system.

In still another embodiment of the present invention, a single dose distributor can be operably connected to both injection needles to deliver the same fluid to both injection needles. Each injection needle also can be operably connected to a separate dose distributor which allows the injection of at least two doses of different fluids, wherein the volume of each fluid dose may be identical or different, and the two fluid doses may be delivered to the recipient bird simultaneously or consecutively.

The reciprocating carrier further typically is driven by a hydraulic or electric actuator mechanism and the dose distributor(s) also will be operably connected to multidirectional flow valve to alternatively draw liquid from the fluid supply container and to expel a desired dose through the respective needle.

Additional objects and aspects of the present invention will become more apparent upon review of the detailed description set forth below when taken in conjunction with the accompanying figures, which are briefly described as follows.

BRIEF DESCRIPTION OF THE DRAWINGS

The present invention will now be exemplified with reference to the following drawings where.

DETAILED DESCRIPTION OF THE PREFERRED EMBODIMENT

Reference now will be made in detail to presently preferred embodiments of the invention, one or more examples of which are illustrated in the accompanying drawings. Each example is provided by way of explanation of the invention, not limitation of the invention. In fact, it will be apparent to those skilled in the art that various modifications, combination, additions, deletions and variations can be made in the present invention without departing from the scope or spirit of the invention. For instance, features illustrated or described as part of one embodiment can be used in another embodiment to yield a still further embodiment. It is intended that the present invention covers such modifications, combinations, additions, deletions and variations as come within the scope of the appended claims and their equivalents.

The injection delivery devices and systems according to the present invention are useful to deliver substantially simultaneously multiple fluid doses to a recipient such as small birds. The devices and systems of the present invention are particularly useful for delivering fluids that cannot be stably stored or mixed together. The injection delivery systems of the present invention also allow the co-delivery of vaccines such as herpes virus of turkey (HVT) vaccine with compositions such as antibiotics that may otherwise reduce the therapeutic efficacy of a live virus vaccine.

Figure 1:
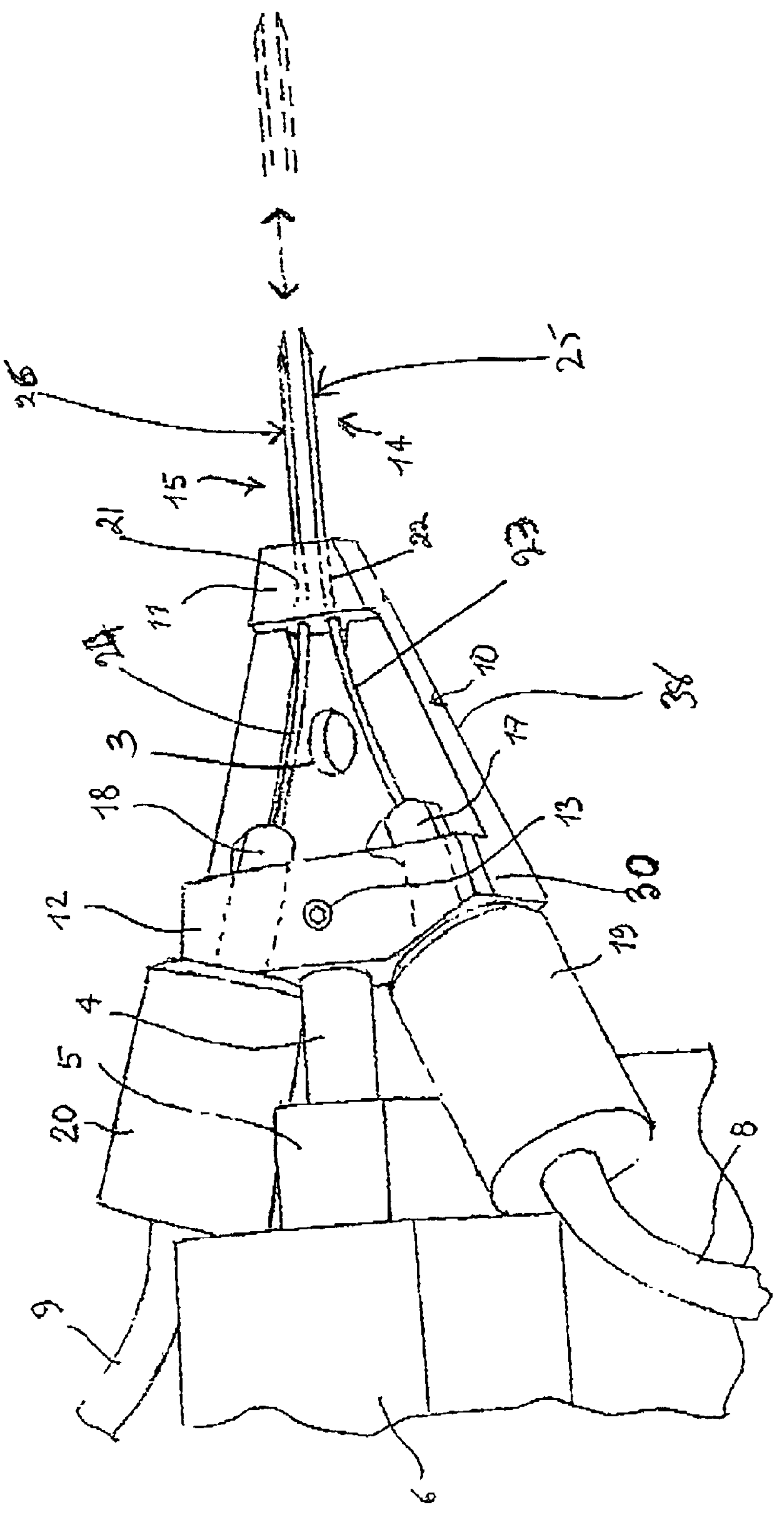
FIG. 1 is a perspective view of the needles assembly of the present invention.

Referring now to FIG. 1, the present invention provides an injection needle support 10 adapted to receive at least two injection needles 14, 15. The injection needle support 10 comprises a base 38 having a base plate 30 and an end plate 11 disposed thereon. The base 38 may be any geometric shape, such as square, rectangular, circular or the like, that will rigidly hold the base plate 30 and the end plate 11 in a fixed spatial relationship. The base 38 may be a solid plate or a frame defining a hole as shown, for example, in FIG. 1.

In preferred embodiments, the base 38 is triangular or trapezoidal, with the end of the base 38 having the end plate 11 thereon being narrower than the end having the base plate 30, as shown in FIG. 1. The end plate 11 has at least two substantially parallel bores 21, 22, each bore capable of receiving a shank 23, 24 of one of the injection needles 14, 15. Suitable injection needles 14, 15 for use in the system of the present invention each generally will comprise a hub or distal end 17, 18 and an injection or proximal end 25, 26 disposed at the opposite end of the shank 23, 24. Preferably, the injection end 25, 26 of each needle is sharpened to ease penetration of the skin of a recipient bird, and further is typically beveled.

The injection needle support 10 of the present invention further comprises recesses 27, 28 in the base plate 30. The recesses 27, 28 are configured to receive the hubs 17, 18 of the injection needles 14, 15 and which may be held in position in the recesses 27, 28 by a releasable or backing plate clamp 12. The claim generally will be secured with a set screw or similar fastener 13 to prevent the needle hubs 17, 18 from disengaging from the recesses 27, 28. Fluid connections 19, 20 provided, and generally are mounted in communication with the recesses 27, 28 and are also able to engage with the hubs 17, 18 held in the recesses 27, 28, thereby allowing fluids to pass into the injection needles 14, 15 from a fluid supply source (not shown).

The injection needles 14, 15 may be attached to the injection needle support 10 by passing the injection end 25, 26 of a injection needle 14, 15 through a bore 21, 22 and placing a hub 17, 18 in a recess 27, 28 of the base plate 30. The clamp 12 is then positioned on the base plate 30 and secured over the needle hubs to prevent the hubs 17, 18 from being displaced from the recesses 27, 28 and the injection needle support 10. In one embodiment of the present invention, the clamp 12 is a detachable plate. In another embodiment, the clamp 12 can be connected to the injection needle support 10 along a hinge mechanism that allows the clamp to the be displaced, but not removed from, the injection needle support 10. Exemplary fasteners for securing the clamp 12 in a closed configuration and which can be easily released to allow the injection needles 14, 15 to be easily replaced when blunted, blocked or otherwise becomes unsuitable for injecting birds include, but are not limited to, a screw means or opposed polarity magnets, and the like.

The injection needles 14, 15 can be replaced by releasing fasteners 13 of the clamp 12, lifting the hub 17, 18 from the recess 27, 28, disconnecting the needles 14, 15 from fluid connectors 19, 20, and extracting the respective needle 14, 15 from the end plate 11 of the needle support. Substitute injection needles 14, 15 may then be introduced to the injection needle support 10 by reversing this order of operation.

In one embodiment of the present invention, the distance separating the recesses 27, 28 from one another exceeds the distance between the bores 21, 22. In such an embodiment, the injection ends 25, 26 of injection needles 14, 15, once placed into position in the injection needle holder 10, generally will remain substantially parallel while the shanks 23, 24 between the hubs 17, 18 and the end plate 11 are curved. However, the shanks 23, 24 preferably are not bent, so as to thus maintain unimpeded fluid flows through the cannula of the needles 14, 15.

Alternatively, the distance separating the recesses 27, 28 can be about, or substantially the same as the distance between the bores 21, 22 of the plate 11 so that the needle shanks 23, 24 are substantially parallel.

In the various embodiments of the injection delivery systems of the present invention, the injection ends 25, 26 of the injection needles 14, 15, when inserted into the injection needle support 10, will project beyond the end plate 11. The extent to which the injection ends 25, 26 project beyond the end plate 11 may be selected manually or automatically according to the type or size of the recipient birds. The selected length of the injection ends 25, 26 of the needles and the degree of the extension movement of the carrier 4 imparted by the actuator 6 also determines whether the injection of fluid(s) into the recipient bird is subcutaneous or intramuscularly by affecting the depth of penetration of the needles. Injection needles 14, 15 suitable for use in the present invention may be from 2–20 gauge. Preferably, the injection ends 25, 26 are sharpened and beveled. For example, beveled injection ends 25, 26 orientated in substantially opposite directions are shown in FIG. 1. This substantially opposed orientation of beveled injection ends 25, 26 can direct injected fluids in divergent directions to reduce potential co-mingling of incompatible fluids within the tissues of the recipient bird.

Figure 2:
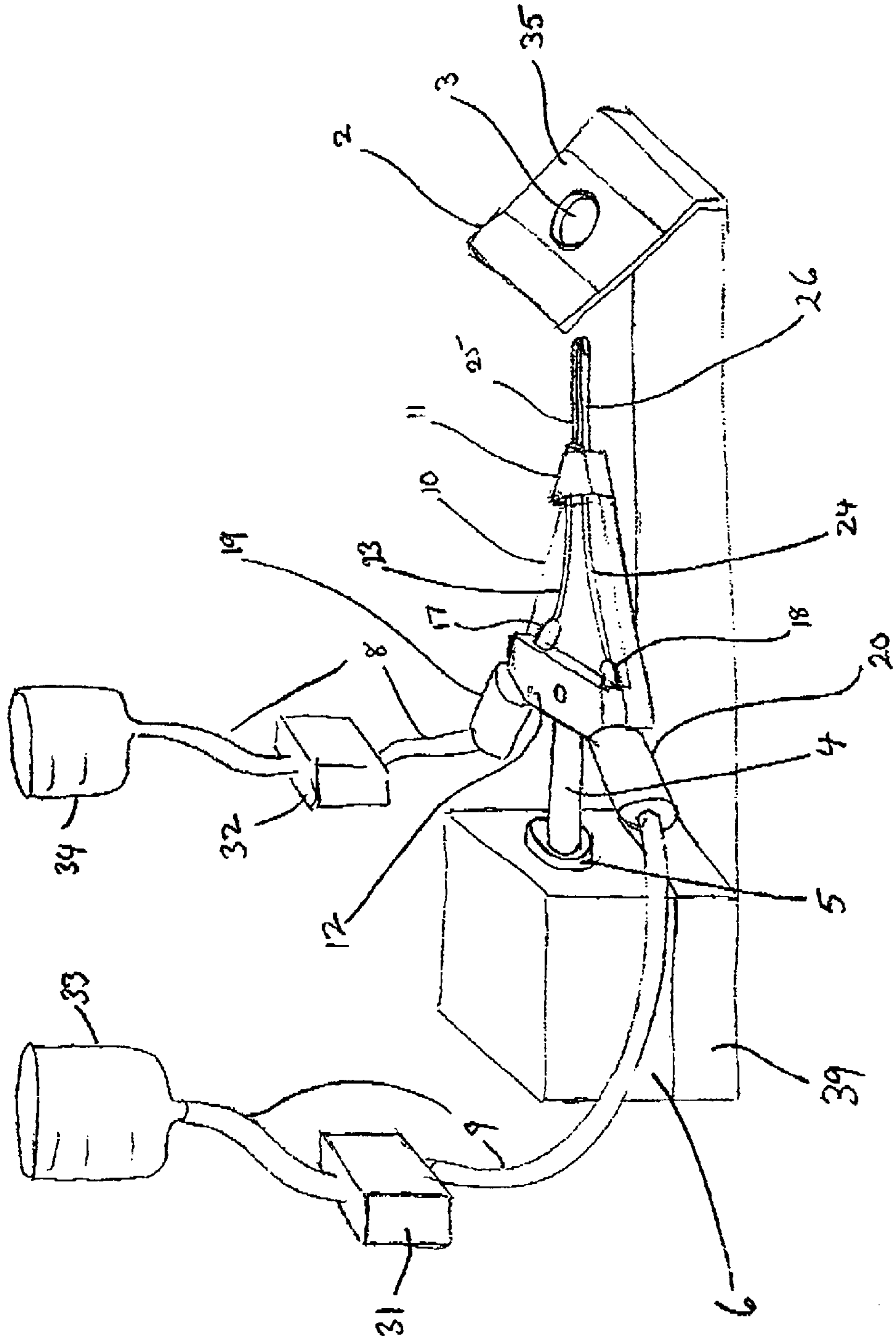
FIG. 2 is a schematic view of the injection delivery system according to the present invention.
Figure 3:
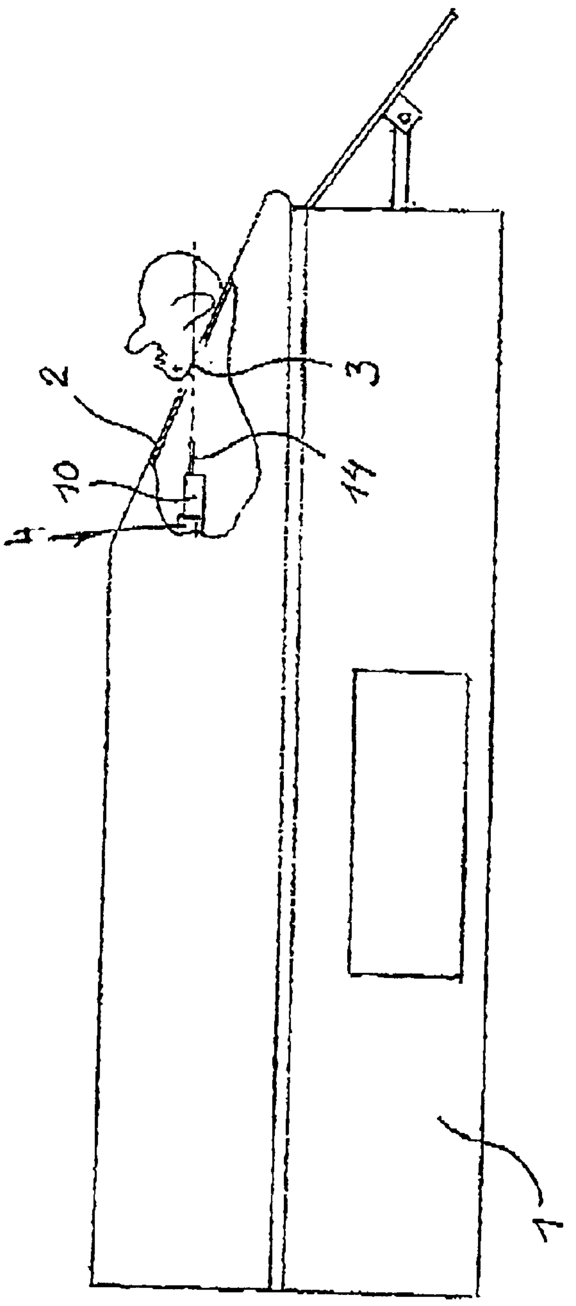
FIG. 3 is a schematic view of an additional embodiment of the injection delivery system according to the present invention

As illustrated in FIGS. 2A and 3, the present invention provides an injection needle support 10 connected to a carrier 4 slidably disposed in a guide 5. The carrier 4 is operably connected to an actuator 6 configured to reciprocally move the carrier 4 and injection needle support 10 from a retracted position to an extended injection position. Suitable actuators 6 include, but are not limited to, a solenoid, electric motor or driver, or a hydraulic actuator, the selected actuator 6 further comprising a power source. The actuator 6 is also operably connected to a switch 35 that may include, but is not limited to, a manually activated switch, or an automatic switch such as a pressure switch or sensor, or a photoelectric switch. It is contemplated that the switch will be reversible so that in a first position the carrier 4 and injection needle support 10 are extended by the actuator 6, and in a second position the carrier 4 and the injection needle support 10 may be retracted away from the injected recipient bird. It is further contemplated that the carrier 4 and the injection needle support 10 may be automatically retracted, for example, by a spring-biased device, for example, once the actuator 6 is deactivated.

The injection delivery system of the present invention further comprises one or more dose distributors 31, 32 communicating with the fluid connectors 19, 20 for the needles 14, 15. Suitable fluid distributors 31, 32 for use in the present invention include, but are not limited to, pumps or syringes, such as a multi-dose syringe and the like that are capable of receiving a fluid dose from fluid containers or supplies 33, 34 and delivering the fluid dose to an injection needle 14, 15. Each fluid container 33, 34 is preferably connected to a dose distributor 31, 32 by a two-way valve 36, 37 that allows a fluid dose to be withdrawn from the fluid container 33, 34 and delivered to the injection needle 14, 15 without back-flow to the fluid container 33, 34.

In one embodiment of the injection delivery system of the present invention, each dose distributor 31, 32 is attached to the carrier 4 or to injection needle support 10 such that the dose distributor 31, 32 will move with the carrier 4 and injection needle support 10. In another embodiment, dose distributors 31, 32 may be separate from the carrier 4 and the injection needle support 10 and connected to the fluid connectors 19, 20 by flexible fluid ducts or lines 8, 9. In these embodiments of the present invention, the fluid container 33, 34 also may be optionally attached to the carrier 4 or injection needles support 10, or attached to a fixed structure such as a housing (FIG. 3). The fluid container 33, 34 likewise can communicate with the dose distributor 31, 32 by a flexible or rigid fluid duct 8, 9. The injection delivery system further generally includes a control means and power source to activate the dose distributors 31, 32 to deliver at least two fluid doses to a bird maintained against the retaining plate 2, and cause movement of the needle support to its operative injection position.

The needle injection device of the present invention further generally includes a retaining plate 2 having an aperture 3 therein. The retaining plate 2 and the aperture 3 are positioned so that when the carrier 4 and the injection needle support 10 are in an extended position, the injection ends 25, 26 project through and beyond the aperture 3 to a selected distance that allows injection of a fluid dose into a recipient bird. The chick or other small bird can be slightly pressed against the retaining plate 2 by the operator or otherwise restrained in a desired position for injection. The retention means also may be sloped with regard to the travel axis of the needles.

In operation of the injection delivery systems of the present invention, a chick or other small bird is maintained against the retaining plate 2 with the area of the bird to receive the fluid dose(s) positioned over the aperture 3 in the retaining plate 2. Generally, the neck of the bird is the targeted area, but any other areas of the bird, including the breast, thigh, wing and the like may be selected to receive the delivered fluid dose. An optional restraint may be used to prevent escape of the bird. Pressure of the bird against the retaining plate 2 can engage and actuate a switch to activate the actuator 6 to move the carrier 4 and the injection needle support 10 attached thereto, to a predetermined extended operative injection position. The injection ends 25, 26 of the needles 14, 15 project through the retaining plate 2 and the aperture 3 therein, to penetrate the skin overlying the selected injection point of the bird.

When the carrier 10 and the needles 14, 15 thereon are in the extended position with the injection 25, 26 ends, in the bird, the dose distributors 31, 32 are actuated by a switch means activated automatically, as described in U.S. Pat. No. 5,312,353 incorporated herein by reference in its entirety, or by a system operator to deliver the fluid doses through their respective needles 14, 15. The volumes for the delivered doses are selected depending on the treatment protocol administered to the birds. A suitable adjustment means, for example, as taught in U.S. Pat. No. 5,312,353 can administer doses from 0.05 to 4 ml per dose. The volumes can be identical or different between needles. It is contemplated to be within the scope of the present invention for the fluid doses delivered to a recipient bird to be the same therapeutic fluids or different. The delivery systems of the present invention can deliver the same fluid to two different positions in the bird or two different fluids that may be incompatible or unstable when mixed.

What is claimed is:

1. An injection needle support, comprising:

(a) a base;

(b) an end plate having at least two substantially parallel bores, wherein each bore is suitable for receiving a shank portion of at least one injection needle;

(c) a base plate having at least two recesses, each recess configured for receiving a hub of the at least one injection needle;

(d) a hub securing clamp for engaging and holding the hub of the needle within its recess; and (e) at least two fluid connections, each fluid connection capable of communicating with the injection needle hub received by one of the recesses of the base plate.

2. The injection needle support according to claim 1, wherein a distance separating the recesses of the base plate greater than a distance separating the bores of the end plate.

3. The injection needle support according to claim 1, further comprising at least two injection needles, the shank portion of each injection needle extending from the hub of the needle to an injection end, the hub of each injection needle being received within one of the recesses at the base, and wherein the injection ends of the injection needles project through the end plate and are arranged substantially parallel.

4. The injection needle support according to claim 3, wherein the injection ends of the injection needles have bevels.

5. The injection needle support according to claim 4, wherein the bevels are oriented in substantially opposite directions.

6. The injection needle support according to claim 3, wherein the shank portions of the injection needles diverge.

7. The injection needle support according to claim 1, wherein the clamp is secured with a fastener.

8. The injection needle support according to claim 1, wherein the clamp and the base plate have contacting surfaces, and further comprising magnets attached to clamp and the base plate for securing the clamp to the base plate.

9. An injection delivery assembly, comprising:

(a) an injection needle support, comprising:

(1) a base;

(2) an end plate having at least two substantially parallel bores, wherein each bore is suitable for receiving a shank portion of at least one injection needle;

(3) a base plate having at least two recesses, each recess configured for receiving a hub of the at least one injection needle;

(4) a hub securing clamp for engaging and holding the hub of the needle within its recess; and (5) at least two fluid connections, each fluid connection capable of communicating with the injection needle hub received by one of the recesses of the base plate, wherein the carrier is slidably mounted on a guide means;

(b) a dose distributor operably communicating with the fluid connection;

(c) a fluid container operably communicating with the dose distributor;

(d) an actuator operably connected to the carrier, the actuator capable of reciprocally moving the carrier and the injection needle support in a direction substantially parallel to the injection ends of the injection needles; and (e) a switch means for activating the actuator.

10. The injection delivery assembly according to claim 9, further comprising a retention plate having an aperture, the aperture arranged so that the injection ends of the injection needles project through the aperture when the carrier and the injection needle support thereon is in an extended position.

11. The injection delivery assembly according to claim 9, further comprising a housing.

12. The injection delivery assembly according to claim 9, further comprising a bird retaining device.

13. The injection delivery assembly according to claim 9, further comprising a controlling means for automatically activating and extending the carrier and injection needle support when a bird is positioned on the retaining plate.

* * * * *